(12) United States Patent
Duindam et al.

(10) Patent No.: US 11,980,344 B2
(45) Date of Patent: May 14, 2024

(54) SYSTEMS AND METHODS FOR INSTRUMENT BUCKLING DETECTION

(71) Applicant: INTUITIVE SURGICAL OPERATIONS, INC., Sunnyvale, CA (US)

(72) Inventors: Vincent Duindam, San Francisco, CA (US); Timothy D. Soper, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 230 days.

(21) Appl. No.: 16/331,657

(22) PCT Filed: Sep. 20, 2017

(86) PCT No.: PCT/US2017/052534
§ 371 (c)(1),
(2) Date: Mar. 8, 2019

(87) PCT Pub. No.: WO2018/057633
PCT Pub. Date: Mar. 29, 2018

(65) Prior Publication Data
US 2019/0239723 A1      Aug. 8, 2019

Related U.S. Application Data

(60) Provisional application No. 62/397,426, filed on Sep. 21, 2016.

(51) Int. Cl.
*A61B 1/00* (2006.01)
*A61B 1/005* (2006.01)
(Continued)

(52) U.S. Cl.
CPC ...... *A61B 1/00149* (2013.01); *A61B 1/00006* (2013.01); *A61B 1/00057* (2013.01);
(Continued)

(58) Field of Classification Search
CPC ............ A61B 1/00057; A61B 1/00131; A61B 1/00133; A61B 1/00135; A61B 1/00147;
(Continued)

(56) References Cited

U.S. PATENT DOCUMENTS 6,380,732 B1    4/2002  Gilboa et al.
6,389,187 B1    5/2002  Greenaway et al.
(Continued)

FOREIGN PATENT DOCUMENTS

CN    101198370 A    6/2008
CN    103874449 A    6/2014
(Continued)

OTHER PUBLICATIONS

Extended European Search Report for Application No. EP17853820.3 dated Apr. 29, 2020, 7 pages.
(Continued)

*Primary Examiner* — Ryan N Henderson
*Assistant Examiner* — Pamela F Wu
(74) *Attorney, Agent, or Firm* — Haynes & Boone, LLP

(57) ABSTRACT

A method comprises measuring, with a sensor, a shape of a section of an elongated flexible instrument and comparing the measured shape of the section of the elongated flexible instrument to an expected shape. The method also comprises determining whether the measured shape of the section of the elongated flexible instrument differs from the expected shape by a predefined threshold.

20 Claims, 7 Drawing Sheets

(51) Int. Cl.
*A61B 1/01* (2006.01)
*A61B 5/00* (2006.01)
*A61B 5/06* (2006.01)
*A61B 34/00* (2016.01)
*A61B 34/35* (2016.01)
*A61B 34/37* (2016.01)
*A61B 34/20* (2016.01)
*A61B 34/30* (2016.01)
*A61B 90/00* (2016.01)

(52) U.S. Cl.
CPC .......... *A61B 1/0016* (2013.01); *A61B 1/009* (2022.02); *A61B 1/01* (2013.01); *A61B 5/065* (2013.01); *A61B 5/6852* (2013.01); *A61B 34/25* (2016.02); *A61B 34/35* (2016.02); *A61B 34/37* (2016.02); *A61B 34/76* (2016.02); *A61B 2034/2051* (2016.02); *A61B 2034/2059* (2016.02); *A61B 2034/2061* (2016.02); *A61B 2034/2065* (2016.02); *A61B 2034/254* (2016.02); *A61B 2034/301* (2016.02); *A61B 2090/065* (2016.02); *A61B 2090/3614* (2016.02); *A61B 2090/371* (2016.02); *A61B 2090/3735* (2016.02); *A61B 2090/374* (2016.02); *A61B 2090/376* (2016.02); *A61B 2090/3762* (2016.02)

(58) Field of Classification Search
CPC .......... A61B 1/00151; A61B 1/00154; A61B 1/00156; A61B 1/0016; A61B 34/25; A61B 34/30; A61B 2034/301–303; A61B 34/37; A61B 34/70; A61B 2034/2051; A61B 2034/2059; A61B 2034/2061; A61B 2034/254; A61B 34/32; A61B 1/00006; A61B 1/00146; A61B 1/005; A61B 1/01; A61B 5/065; A61B 5/6852; A61B 1/00055; A61B 1/0051; A61B 1/00071; A61B 1/012; A61B 1/0125; A61B 1/018; A61B 1/00062; A61B 1/00073–00078; A61B 1/00142; A61B 1/00158–008
USPC .................. 600/118, 114, 117, 121
See application file for complete search history.

(56) References Cited

U.S. PATENT DOCUMENTS

| | | | |
|---|---|---|---|
| 7,316,681 | B2 | 1/2008 | Madhani et al. |
| 7,772,541 | B2 | 8/2010 | Froggatt et al. |
| 8,900,131 | B2 | 12/2014 | Chopra et al. |
| 9,259,274 | B2 | 2/2016 | Prisco et al. |
| 9,452,276 | B2 | 9/2016 | Duindam et al. |
| 10,206,747 | B2 | 2/2019 | Fenech et al. |
| 2005/0234293 | A1* | 10/2005 | Yamamoto ............ A61B 34/70 600/102 |
| 2006/0013523 | A1 | 1/2006 | Childers et al. |
| 2008/0218770 | A1 | 9/2008 | Moll et al. |
| 2008/0287963 | A1* | 11/2008 | Rogers ............... A61B 1/00042 606/130 |
| 2009/0324161 | A1 | 12/2009 | Prisco |
| 2011/0319714 | A1 | 12/2011 | Roelle et al. |
| 2012/0203168 | A1* | 8/2012 | Fujimoto ............... G01L 5/105 604/95.01 |
| 2013/0096572 | A1 | 4/2013 | Donhowe et al. |
| 2013/0204124 | A1* | 8/2013 | Duindam ............ A61B 10/0233 604/272 |
| 2014/0343568 | A1* | 11/2014 | Fenech ............... A61B 34/71 606/130 |
| 2015/0297864 | A1* | 10/2015 | Kokish ............... A61B 34/30 604/95.04 |
| 2015/0367508 | A1 | 12/2015 | Hatakeyama |
| 2016/0067450 | A1 | 3/2016 | Kowshik |
| 2016/0184032 | A1* | 6/2016 | Romo ................... A61B 10/04 606/130 |
| 2017/0265953 | A1 | 9/2017 | Fenech et al. |
| 2018/0084974 | A1* | 3/2018 | Wake ................. A61B 1/00154 |
| 2019/0247128 | A1 | 8/2019 | Inouye et al. |

FOREIGN PATENT DOCUMENTS

| | | |
|---|---|---|
| EP | 2767211 A1 | 8/2014 |
| EP | 2766083 B1 | 5/2019 |
| JP | H05211991 A | 8/1993 |
| JP | 2009542419 A | 12/2009 |
| JP | 2013017785 A | 1/2013 |
| JP | 2014533996 A | 12/2014 |
| WO | WO-2013056006 A2 | 4/2013 |
| WO | WO-2013116140 A1 | 8/2013 |
| WO | WO-2015089013 A1 | 6/2015 |

OTHER PUBLICATIONS

International Search Report and Written Opinion for Application No. PCT/US2017/052534, dated Jan. 16, 2018, 15 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2017/052534, dated Apr. 4, 2019, 14 pages.

* cited by examiner

SYSTEMS AND METHODS FOR INSTRUMENT BUCKLING DETECTION

RELATED APPLICATIONS

This patent application is the U.S. national phase of International Application No. PCT/US2017/052534, filed Sep. 20, 2017, which designated the U.S. and claims priority to and the benefit of the filing date of U.S. Provisional Patent Application 62/397,426 entitled "SYSTEMS AND METHODS FOR INSTRUMENT BUCKLING DETECTION," filed Sep. 21, 2016, all of which are incorporated by reference herein in their entirety.

FIELD

The present disclosure is directed to systems and methods for navigating a medical instrument into an entry point of a patient, and more particularly to systems and methods for localizing the entry point.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical instruments (including surgical, diagnostic, therapeutic, or biopsy instruments) to reach a target tissue location. As such medical instruments are inserted into the entry point, the section of the medical instrument outside the entry point may be prone to buckling. It is desirable to use methods and systems that mitigate such buckling in order to provide improved use of the medical instruments.

SUMMARY

The embodiments of the invention are summarized by the claims that follow the description.

Consistent with some embodiments, a method comprises measuring, with a sensor, a shape of a section of an elongated flexible instrument and comparing the measured shape of the section of the elongated flexible instrument to an expected shape. The method also comprises determining whether the measured shape of the section of the elongated flexible instrument differs from the expected shape by a predefined threshold.

Consistent with some embodiments, a method comprises manipulating with an instrument drive mechanism, an elongated flexible instrument and measuring, with a sensor, a shape of a section of the elongated flexible instrument. The section of the elongated flexible instrument being between a distal portion of the elongated flexible instrument and a proximal instrument portion. The method further comprises determining, with a control system in communication with the sensor, whether the shape of the section of the elongated flexible instrument buckles beyond a predefined threshold.

Consistent with some embodiments, a system comprises an instrument drive system, an elongated flexible instrument connected to the instrument drive system, and a sensor associated with the elongated flexible instrument to measure a shape of the elongated flexible instrument. The system also comprises a shape constraint mechanism positioned to constrain the elongated flexible instrument at a section between the instrument drive system and a distal end of the elongated flexible instrument and a control system configured to manipulate the elongated flexible instrument using the instrument drive mechanism and to determine whether the section of the elongated flexible instrument within at least a portion of the shape constraint mechanism buckles beyond a predefined threshold.

Consistent with some embodiments, a system comprises a first catheter connected to a first instrument drive system, a first sensor associated with the first catheter to measure a first shape of the first catheter, and a first shape constraint mechanism positioned to constrain the first catheter at a first catheter section between the first instrument drive system and a distal end of the first catheter. The system also comprises a second catheter connected to a second instrument drive system and sized to slideably receive a length of the first catheter and a control system configured to manipulate the first catheter using the first instrument drive mechanism and determine whether the first catheter section within the first shape constraint mechanism buckles beyond a first predefined threshold.

Consistent with some embodiments, a system comprises an outer catheter, an inner catheter including a section sized to extend within and slide relative to at least a portion of the outer catheter, a sensor associated with the inner catheter to measure a shape of the inner catheter, and a control system configured to determine whether the section of the inner catheter buckles beyond a predefined threshold.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 1:
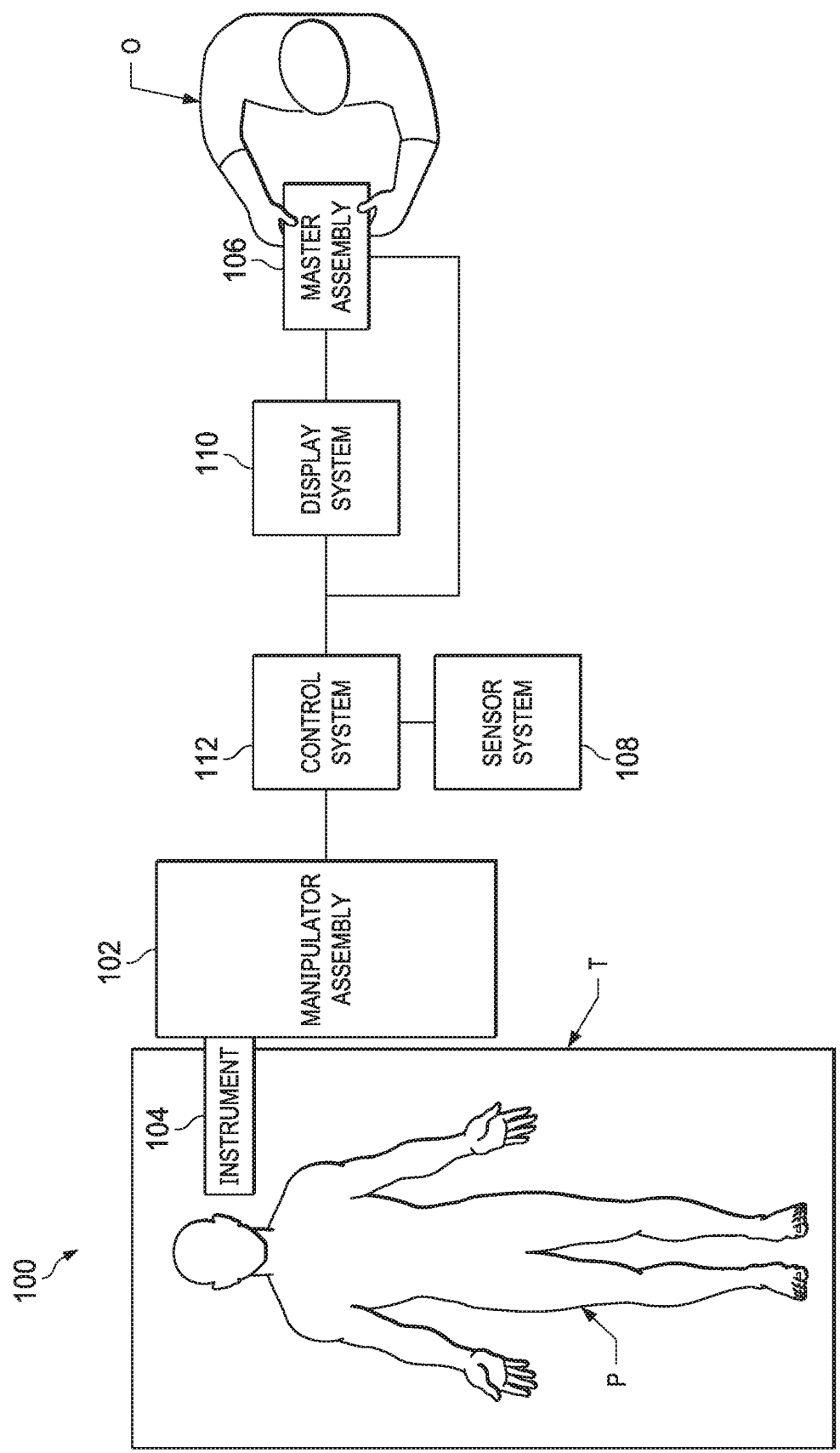
FIG. 1 is a simplified diagram of a teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator O (e.g., a surgeon, a clinician, or a physician as illustrated in FIG. 1) to view the interventional site and to control teleoperational manipulator assembly 102.

Master assembly 106 may be located at a user station such as a physician's console which is usually located in the same room as operating table T, such as at the side of a surgical table on which patient P is located. However, it should be understood that operator O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of an operator that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system.

Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figures 2A, 2B:
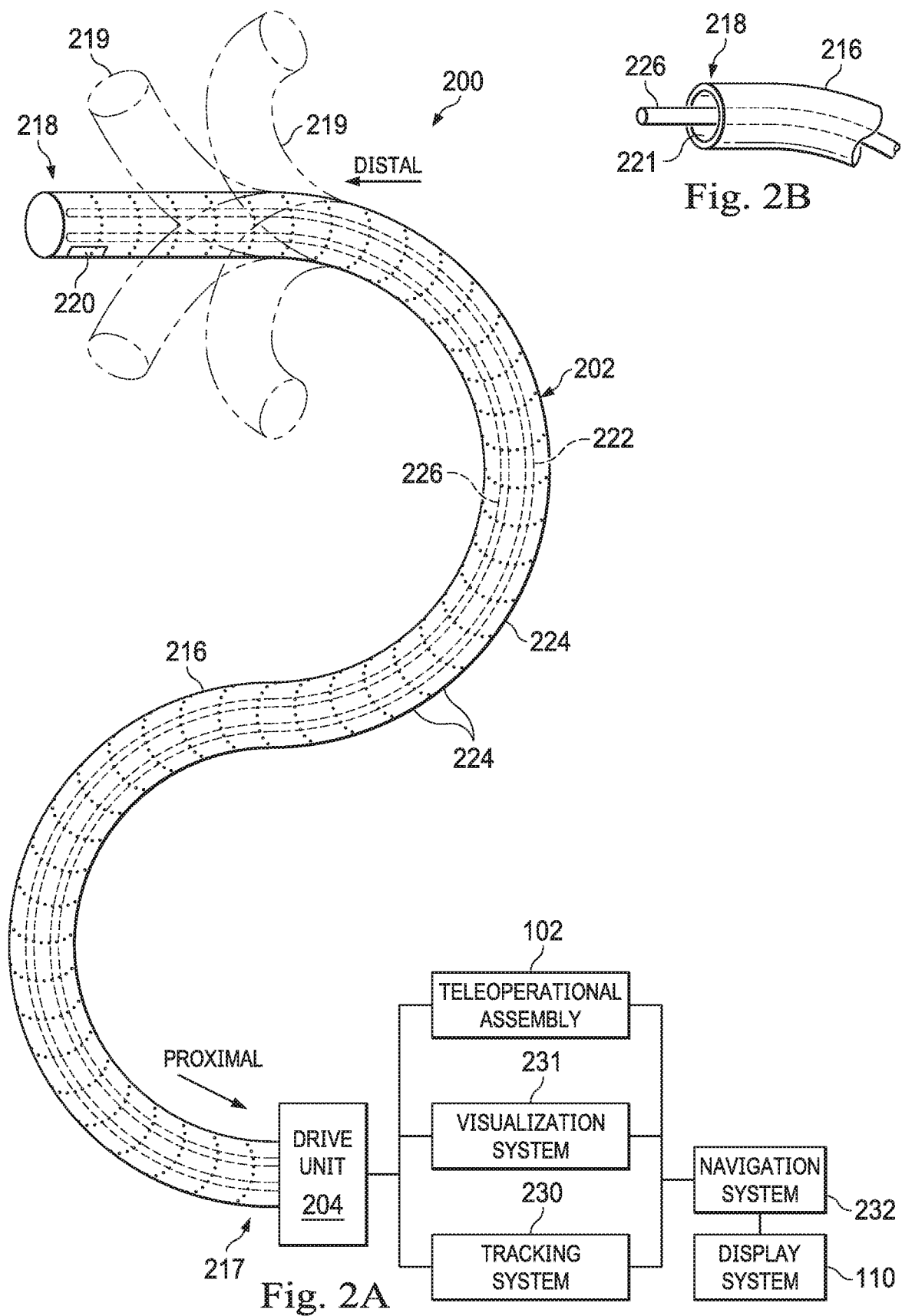
FIG. 2A is a simplified diagram of a medical instrument system according to some embodiments.
FIG. 2B is a simplified diagram of a medical instrument with an extended medial tool according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 µm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 218. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator or other operator with real-time position information. In some examples, the real-time position information may be displayed on display system 110 of FIG. 1 for use in the control of medical instrument system 200. In some examples, control system 112 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

Figure 3A:
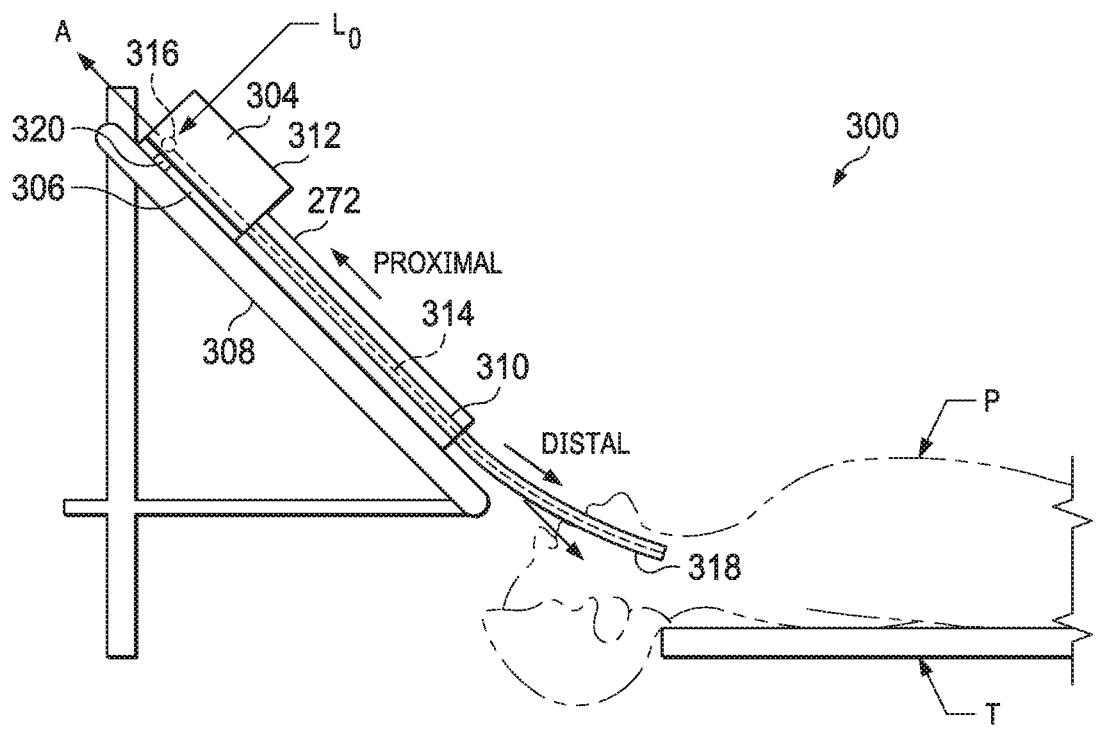
FIGS. 3A and 3B are simplified diagrams of side views of a patient coordinate space including a medical instrument mounted on an insertion assembly according to some embodiments.
Figure 3B:
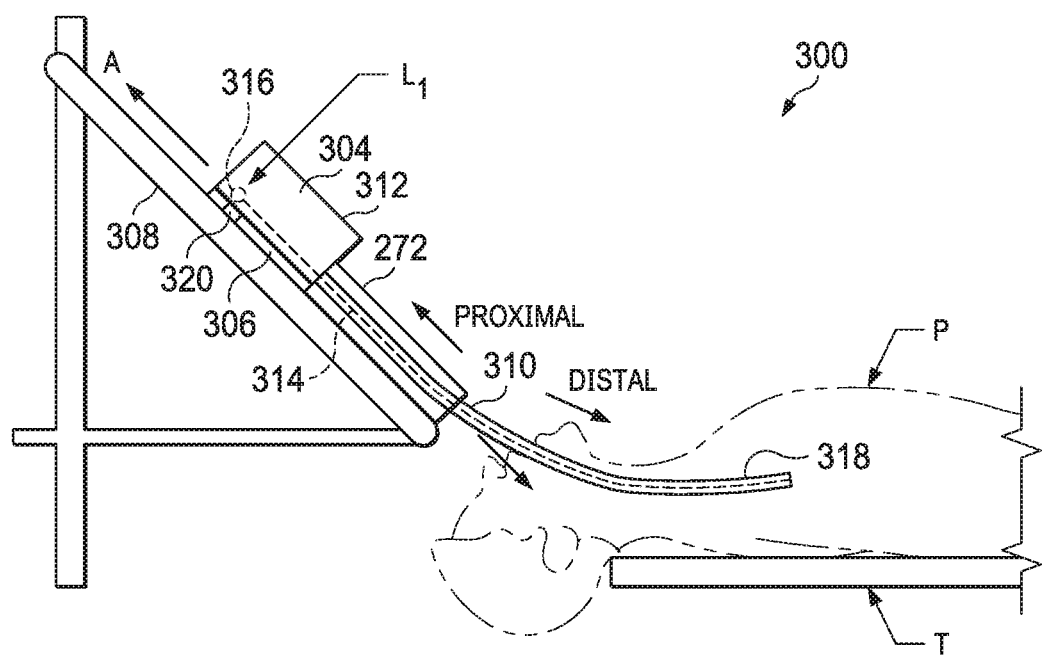

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on platform T. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position L0 on axis A. In this position along insertion stage 308 a component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or another reference value (e.g., I=0). A collapsible shape constraint device 272 supports the elongate device 310 between the instrument body 312 and the entry orifice of patient P. The collapsible shape constraint device 272 constrains the flexible elongate device 310 to a narrow channel defined by the shape constraint device and supports the instrument body against buckling when the instrument body is pushed forward (distally) along the axis A. Consistent with the embodiments of this disclosure, a device may be considered to buckle if it exhibits a non-linear shape, particularly a non-linear shape that exceeds a predefined threshold. The predefined threshold need not be associated with an immediate mechanical failure but may be a shape associated with reduced accuracy, reduced control, predicted failure, or other sub-optimal performance. The predefined threshold may be dependent upon another measurement such as the insertion distance, detection of friction, detection of an obstruction, detection of distal end curvature, or the planned navigation route.

In FIG. 3B, instrument body 312 and instrument carriage 306 have advanced along the linear track of insertion stage 308 and distal end 318 of elongate device 310 has advanced into patient P. In this advanced position, the proximal point 316 is at a position L1 on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position Lx of proximal point 316 relative to position L0. In some examples, position Lx may further be used as an indicator of the distance or insertion depth to which distal end 318 of elongate device 310 is inserted into the passageways of the anatomy of patient P.

The collapsible shape constraint device 272 helps prevent buckling of the flexible elongate device 310 as the instrument body 312 is advanced toward the patient entry orifice. The length of the flexible elongate device 310 housed within the device 272 has an expected straight linear shape. The shape of the flexible elongate device 310 within the device may be measured by the shape sensor 314. If the measured shape of the shape sensor 314 exhibits a non-linear shape or buckle that exceeds a predefined threshold, an error may be reported indicating that the shape constraint device has failed to maintain an expected configuration for the flexible elongate instrument, and thus the shape sensor.

Figure 4A:
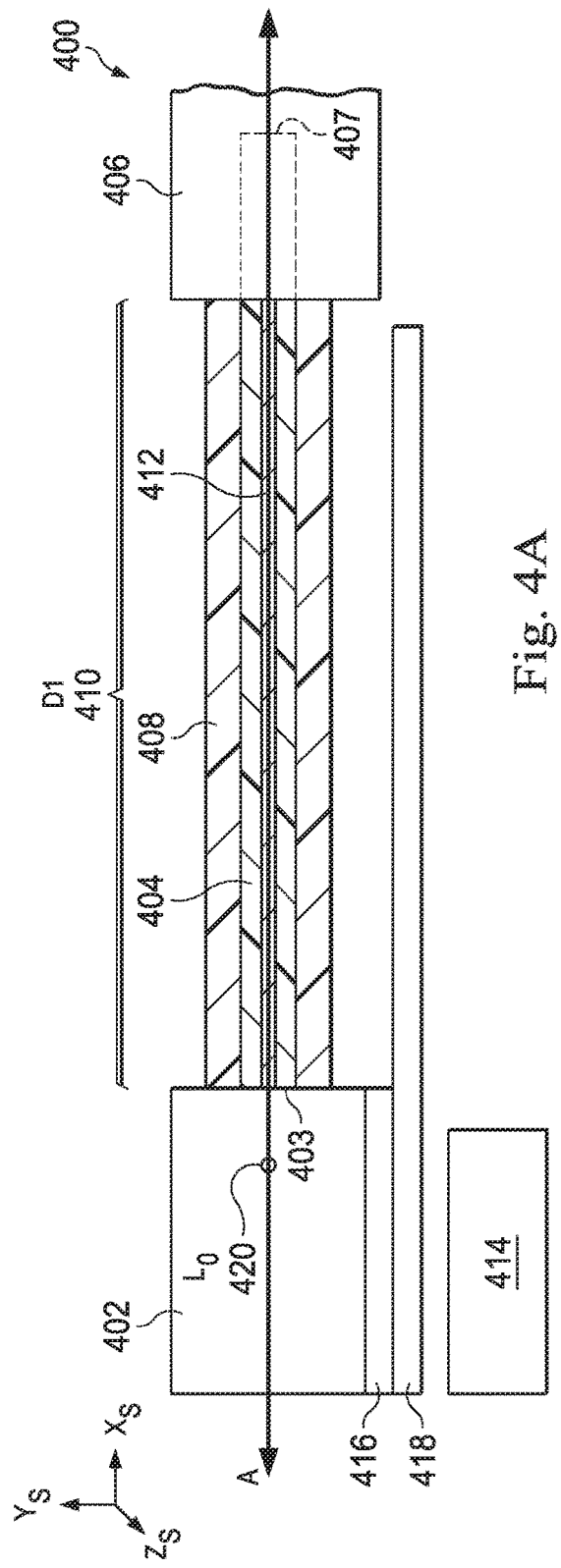
FIGS. 4A and 4B illustrate a view of a surgical coordinate space that includes an elongated flexible instrument positioned within a shape constraint mechanism, according to one example of principles described herein.
Figure 4B:
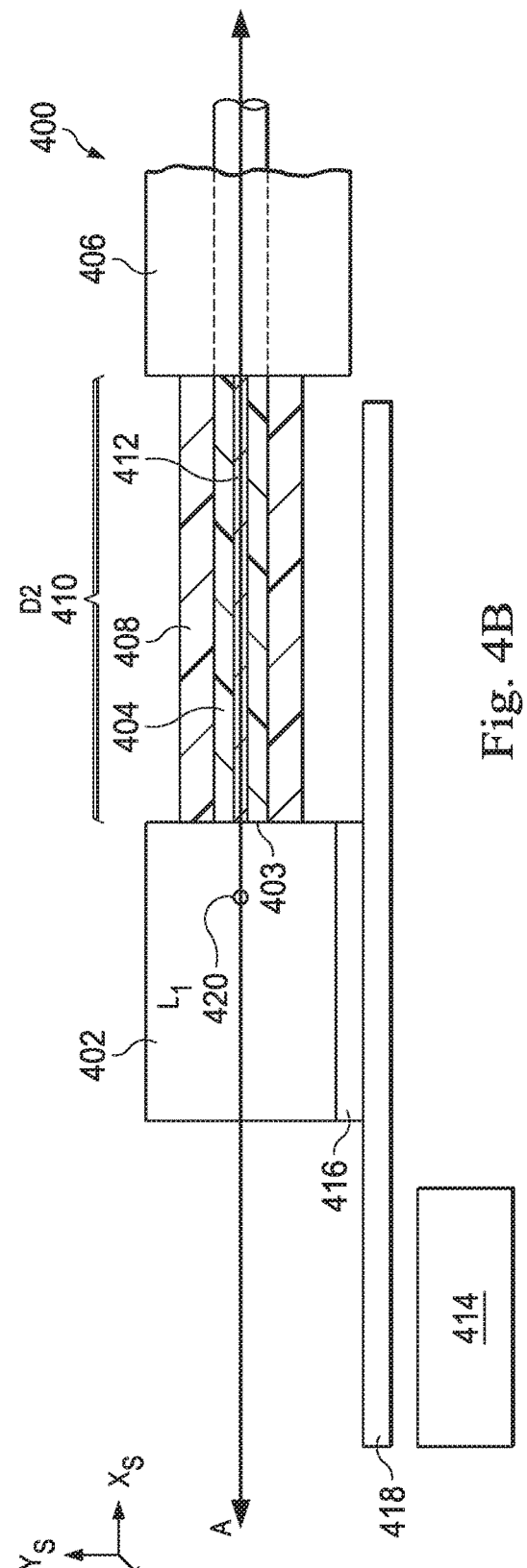

FIGS. 4A and 4B illustrate a view of a surgical coordinate space 400 that includes a flexible elongate instrument 404 (e.g., device 310, 202) positioned within a shape constraint device 408. As previously described, the flexible elongate instrument may be a catheter. The shape constraint device 408 may contract as the catheter is inserted into an entry port 406 and expand as the catheter is retracted from the entry port. The catheter 404 is coupled to an instrument body 402. The catheter 304 also includes a shape sensor 412. The FIG. 4A illustrates the shape constraint device 408 in an expanded position while FIG. 4B illustrates the shape constraint device in a contracted position.

The shape sensor 412 generates shape data that can be used to determine the shape of the catheter 404. The shape data may be used to determine the pose of the distal end 407 of the catheter 404 within the surgical coordinate space 400. For example, if the location of a particular portion of the catheter 404 is known or tracked in the surgical coordinate space 400 (i.e., the base 403 of the catheter 404), then the shape data can be used to determine the location of any point along the catheter 304 in the surgical coordinate space 400. Various shape sensing systems may be used alternatively or in combination to generate the shape data.

In one example, the shape sensor 412 is a fiber optic shape sensor. Such a shape sensor may include one or more fiber-optic cables extending along the length of the catheter 404. The fiber-optic shape sensor may include one or more optical cores. In some cases, the fiber-optic shape sensor may include one or more optical fibers, each optical fiber having one or more optical cores. As described above, the core may include Fiber Bragg Gratings to provide strain measurements in one or more dimensions. In other alternatives, sensors employing other strain sensing techniques may be suitable. In one example, the fiber-optic shape sensor utilizes an interrogation system (not shown) that is positioned proximally of the base 403 of the catheter 404. In operation, the interrogation system generates light and detects returning light to determine the current shape of the fiber-optic shape sensor. The interrogation system may then create data representing the detected light. This data may be analyzed to determine the position and orientation of any point along the length of the catheter 404. Because the base 403, acting as a reference fixture, may have a fixed, known, or tracked position in the surgical coordinate space 400, the position and orientation of any point along the catheter 404 relative to the surgical coordinate space may be determined from the sensor data.

In one example, the shape sensor 412 includes a plurality of electromagnetic (EM) sensors along the length of the catheter 404. As described above, an EM sensor may include one or more conductive coils that may be subjected to an electromagnetic field that is generated by an EM emitter (not shown). Each coil of the EM sensor then produces an induced electrical signal having characteristics that depend on the position and orientation of the coil relative to the electromagnetic field generated by the EM emitter. Thus, the EM sensors may measure six degrees of freedom, e.g., three position coordinates X, Y, Z and three orientation angles indicating pitch, yaw, and roll of a base point or to measure five degrees of freedom, e.g., three position coordinates X, Y, Z and two orientation angles indicating pitch and yaw of a base point.

In one example, the shape sensor 412 includes optical markings for analysis of imaging data obtained by a video camera system. For example, a plurality of video or still cameras may be directed at the portion 410 of the catheter 404 that is outside the entry port 406. The cameras may be stereoscopic in order to obtain data representing the position of the catheter 404 within the surgical coordinate space 400. The optical markings may include varying color, reflectivity, texture, or other features that may allow for more efficient analysis of the imaging data produced by the video camera.

The instrument body 402 may be substantially similar to body 312 and is connected to an instrument carriage 416 which may be part of a teleoperational manipulator assembly (e.g. assembly 102) that is movable within the surgical coordinate space along an insertion stage 418 to cause the catheter 404 to be inserted and retracted from the entry port 406. The teleoperational manipulator assembly may be part of a teleoperational system (e.g., system 100) that includes a control system 414 having processors and memory as well as the software (machine readable instructions) to operate the catheter 404. For example, the control system may manipulate the motors that control movement of the instrument drive mechanism 402 as well as the motors that control the pull-wires and other mechanisms that manipulate the distal end of catheter 404. The control system 414 may also process data obtained from the shape sensor 412 to determine the shape of the catheter 404 in real time.

The catheter 404 may be inserted into a natural orifice of the patient or a surgically created incision. The entry port 406 may be, for example, an endotracheal tube in the case that the orifice is the patient's mouth. The entry port 406 may be, for example, a trocar cannula in the case that the orifice is a surgically created incision.

The shape constraint device 408 is positioned between the instrument body 402 and the entry port 406. The shape constraint device 408 may limit buckling as the catheter 404 is inserted into the entry port 406. Various types of shape constraint devices may be used in accordance with principles described herein. For example, the shape constraint device 408 may include a series of linkages as described in U.S. Provisional Patent Application 61/823,666 filed May 15, 2013 and entitled "Guide Apparatus for Delivery of a Flexible Instrument and Methods of Use," which is hereby incorporated by reference in its entirety. In some examples, the shape constraint device 408 may include a series of retention members and a series of support members as described in U.S. Provisional Patent Application No. 62/029,917 filed Jul. 28, 2014 and entitled Guide Apparatus for Delivery of a Flexible Instrument and Methods of Use" and in U.S. Provisional Patent Application No. 62/359,957 filed Jul. 8, 2016 and entitled "Guide Apparatus For Delivery Of An Elongate Device And Methods Of Use" which are hereby incorporated by reference in their entirety.

The shape constraint device 408 generally helps to prevent buckling, sagging, or other non-linear formations of the catheter 404, however, to prevent the build-up of friction between the catheter and the device, the device may be sized slightly larger than the catheter (e.g., 2-10 mm.). Because of the size differential, in the advanced position, the catheter 404 may not maintain an exactly linear shape and, consequently the portion of the catheter 404 that is outside the entry port 406 may be longer than the length D1. Shape sensor data from sensor 412 may be used to determine the shape of the catheter 404 over the length D1. If the determined shape exceeds an expected (generally linear) shape by a threshold value, the system 414 may execute an action such as a user warning, a feedback signal to halt further advancement, or an applied force to correct the shape.

The control system 414 may be used to determine the minimum length of the portion 410 of the catheter 404 that is outside the entry port 406. As shown in FIG. 4B, the length of the portion 410 becomes smaller as the catheter 404 is inserted into the entry port 406. Various techniques may be used to determine the minimum length of the portion 410 at any given time during operation of the catheter 404. In one example, data from an insertion sensor (e.g. an encoder) associated with a motor of the instrument carriage 416 that drives the catheter 404 may be used to determine the minimum length of the portion 410. For example, in a retracted position, a proximal point 420 on the instrument body 402 is at a position $L_0$ on axis A. In this position along insertion stage 418 a component of the location of proximal point 420 may be set to a zero and/or another reference value to provide a base reference to describe the position of instrument carriage 416, and thus proximal point 420, on insertion stage 418. With this retracted position of instrument body 402 and instrument carriage 416, the distal end 407 of flexible elongate instrument 404 may be positioned just inside the entry port 406. In this retracted position, the minimum length of the portion 410 outside the entry port 406 is a length D1. If the instrument 404 is generally unbuckled, the minimum length of the portion 410 may be approximately the same as the minimum length of the portion 410 Also in this position, the insertion sensor may be set to an initial valued (e.g., zero and/or another reference value). In FIG. 4B, instrument body 402 and instrument carriage 416 have advanced along the insertion stage 418 and the distal end of flexible elongate instrument 404 has advanced through the entry port 406. In this advanced position, the proximal point 420 is at a position $L_1$ on the A-axis. Data from the insertion sensor indicates the distance between $L_0$ and $L_1$. More specifically, data from an encoder sensor may indicate the change of the motor state. The state of the motor may include the current rotational position of a motor as well as the number of turns the motor has made from a reference state. The minimum length of the portion 410 outside the entry port 406 is a length D2 which is approximately the length D1 minus the advanced distance between $L_0$ and $L_1$. If the portion 410 outside the entry port 406 is buckled, the actual length of the portion 410 may exceed the length D2.

The control system 414 may analyze the shape of the catheter 404 during operation of the catheter. For example, the control system analyzes data from the shape sensor 412 to determine the current shape of the catheter 404. The control system 414 then compares the shape data received from the shape sensor with an expected shape. Various techniques may be used to define the expected shape. For example, as will be described in further detail below, comparing the shape data with an expected shape may involve determining whether the current shape of the catheter 404 exceeds an expected boundary. Comparing the shape data with an expected shape may also involve determining that a portion of the catheter has deviated from the axis A by a predefined distance. Comparing the shape data with an expected shape may also involve determining directional movement of the catheter 404 in a direction orthogonal to the insertion direction.

If the control system 414 determines that the current shape differs from the expected shape by a predetermined amount, then the control system may trigger a buckling mitigation action. In one example, a buckling mitigation action involves reporting a warning or error message to an operator the catheter 404. In one example, the buckling mitigation action involves transitioning the catheter control system to a safe state. The safe state is one in which further movement of the catheter is prohibited. In some examples, the buckling mitigation action may involve indicating to the user the precise portion of the catheter 404 that has exceeded the expected shape. In some examples, the buckling mitigation action may include automatically retracting or adjusting the position of the catheter 404 until the current shape of the catheter 404 returns to a state that is closer to the expected shape. In one example, the buckling mitigation action may include modifying the shape of the shape constraint device to reduce the measured buckling. For example, the shape constraint device may be controlled to deform in a direction opposite the measured buckling to cause the catheter to return to the expected shape. Alternatively, if the catheter is buckling due to friction with the constraint device, the constraint device may be rotated about its longitudinal axis to overcome the static friction.

Figure 5:
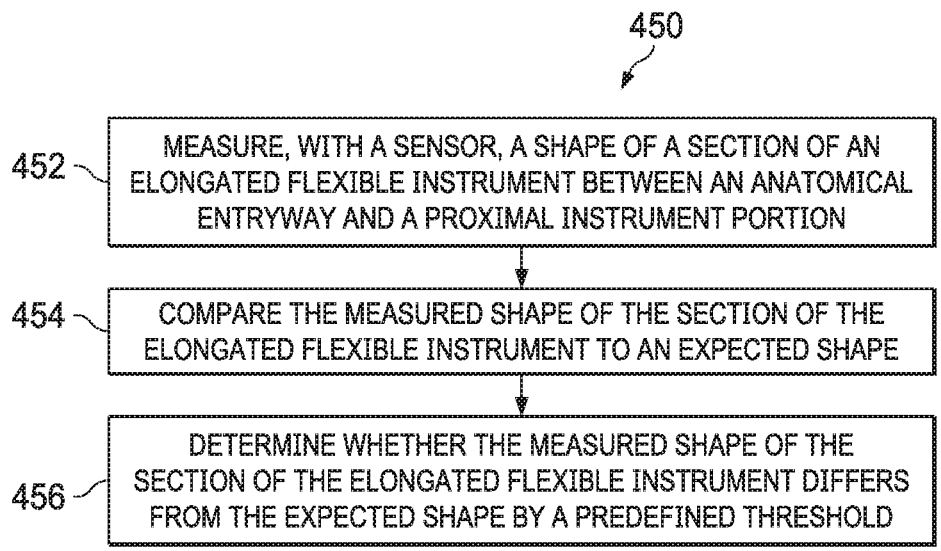
FIG. 5 is a flowchart showing an illustrative method for detecting buckling of the elongated flexible instrument, according to one example of the present disclosure.

FIG. 5 is a flowchart showing an illustrative method 450 for detecting buckling of the elongated flexible instrument. The method 450 is illustrated in FIG. 5 as a set of operations or processes 452-456. Not all of the illustrated processes 452-456 may be performed in all embodiments of method 450. Additionally, one or more processes that are not expressly illustrated in FIG. 5 may be included before, after, in between, or as part of the processes 452-456. In some embodiments, one or more of the processes may be implemented, at least in part, in the form of executable code stored on non-transitory, tangible, machine-readable media that when run by one or more processors (e.g., the processors of control system 112 or 414) may cause the one or more processors to perform one or more of the processes.

According to the present example, the method 450 includes a step 452 for measuring, with a sensor, a shape of a section of an elongated flexible instrument between an anatomical entryway, such as an entry port 406 at a patient's mouth or a cannula at a surgically created opening, and a proximal instrument portion such as the instrument body 402. The sensor may be, for example, a fiber optic shape sensor, a series of EM sensors, or an imaging sensor. The method 450 further includes a step 454 for comparing the measured shape of the section of the elongated flexible instrument to an expected shape. The expected shape may be a line corresponding to a reference axis such as a central axis or base axis through a shape constraint device such as an anti-buckling mechanism 408 that is placed between the anatomical entryway and the proximal instrument portion. Alternatively, the expected shape may be a shape having a predefined cumulative deviation from an axis such as the central or base axis. Alternatively, the expected shape may be any shape that fits within a predefined volume. Alternatively, the expected shape may be a shape wherein the distal end is an expected distance from a proximal end. The method 450 further includes a step 456 for determining whether the measured shape of the section of the elongated flexible instrument differs from the expected shape by a predefined threshold. Optionally, the method may further include triggering a mitigation action, such as providing a warning to an operator, applying a corrective force via the teleoperational system, entering a safe state, or providing instructions for corrective action to a user.

Figure 6A:
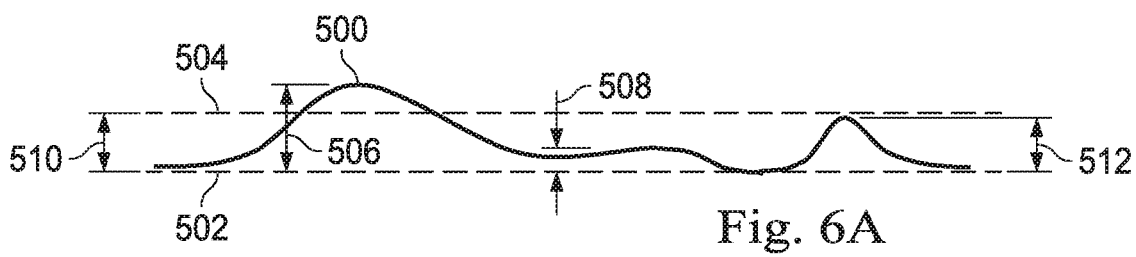
FIGS. 6A and 6B illustrate shape data sets for use in detecting buckling of an elongate flexible instrument.

FIG. 6A illustrates shape data 500 obtained from a shape sensor such as sensor 412 within a section of a flexible instrument between an entry port and a proximal instrument body. In one example, this section may be constrained by a shape constraint device 408. Axis 502 is an expected shape of the section. In various examples, the expected shape 502 may represent a central axis through a shape constraint device 408 or a base axis along the gravitational bottom of the shape constraint device. A predefined threshold 504 is set at a distance 510 from the expected shape 502 based upon the conformity to the expected shape to needed to achieve the desirable insertion movement accuracy. This threshold may be constant along the length of the shape or vary depending on the expected amount of deviation at different points along the expected shape. In this example, the shape data 500 has a deviation 506 that exceeds the predefined threshold 504. Thus, deviation 506 will trigger a mitigation action. In this example, the shape data 500 also has deviations 508, 512 that are each less than the predefined threshold 504. Neither deviation 508 nor deviation 512 on their own will trigger a mitigation action. In one example, the cumulative magnitude of deviations 508 and 512 may exceed the predefined threshold 504. This cumulative deviation may trigger a mitigation action.

The predefined threshold may be variably dependent upon a measurement or upon a known or detected condition. For example, the catheter may be expected to bend inside a shape constraint device when experiencing friction inside the anatomic passageways due to an obstruction or a tortuous path. Under such conditions, the predefined threshold may be widened. For example, the threshold may be increased when a high input force is measured with a sensor or with reference to insertion motor currents. For example, the threshold may be increased when a distal end of the catheter has a sufficiently curved shape within the patient anatomy. For example, the threshold may be increased when the planned navigation path is predicted to be tortuous.

In some examples, the buckling mitigation action is triggered if one deviation exceeds another deviation by a predetermined value. In one example, the buckling mitigation action is triggered if a deviation 506 is greater than any other deviation 508, 512 by a predetermined value. In some examples, the buckling mitigation action is triggered if a particular deviation 506 exceeds a more distal deviation 508 or deviation 512 by the predefined value.

Figure 6B:
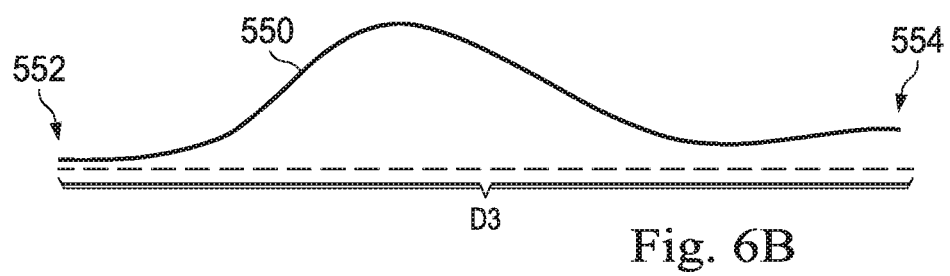

FIG. 6B illustrates an alternative technique for determining whether a measured shape of a section of a flexible instrument differs from an expected shape measurement. As previously described, encoders or other position sensors may be used to determine the distance advanced by the proximal instrument body 402 (i.e., distance between $L_O$ and $L_1$). In this example, shape data 550 is obtained from shape sensor 412. The proximal end 552 of the shape data 550 may correspond to a fixed point relative to the proximal instrument body 402 (e.g., point 420 or catheter end 403. The distal end 554 of the shape data 550 may correspond to a distal end 407 of the catheter or a distal end of the portion 410 of the catheter 404 that is outside the entry port 406. The distal end 554 of the shape data 550 may be determined by a perturbation in shape caused by the entry port 406, a change in temperature at the entry port 406 or other indicator that the catheter has entered the entry port. If the linear distance D3 between the data points 552 and 554 is less than the distance between $L_O$ and $L_1$, this comparison may indicate the catheter 404 has experienced a buckling. If the distance D3 exceeds the distance between $L_O$ and $L_1$ by a predetermined threshold, a mitigation action may be triggered to, for example, alert the user of the buckling or to correct the buckling.

Figure 7A:
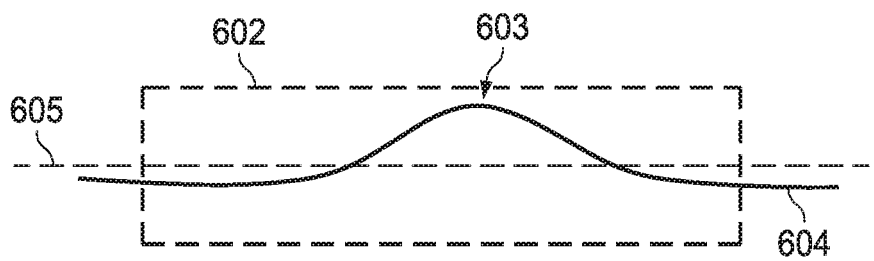
FIGS. 7A and 7B illustrate shape data sets with an expected boundary that may be used for detecting buckling of the elongated flexible instrument, according to one example of principles described herein.
Figure 7B:
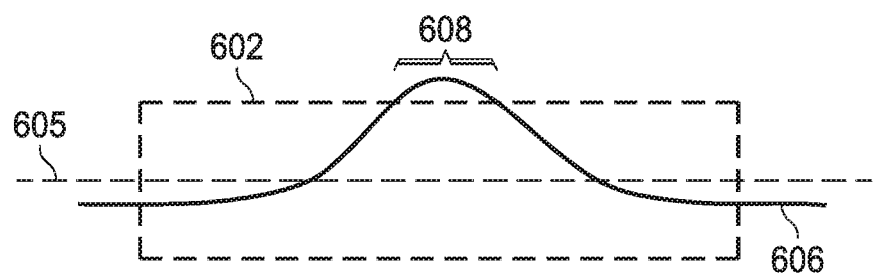

FIGS. 7A and 7B illustrate an expected boundary 602 that may be used for detecting buckling of an elongated flexible instrument 604 (e.g. an instrument 404). The expected shape of method 450 may be any shape that fits within a three-dimensional volume defined by boundary 602. In one example, the expected boundary 602 defines a volume within the surgical coordinate space 400 that corresponds to the volume defined by the shape constraint device 408. The volume may have a substantially tubular shape. The tubular shape may be substantially straight or arcuate. In some implementations, the volume defined by the expected boundary 602 may substantially match the volume defined by the shape constraint device 408. In some implementations, the volume defined by the expected boundary 602 may be scaled slightly larger than or slightly smaller than the volume defined by the shape constraint device 408. The expected boundary 602 may be defined relative to an axis 605 along which the elongated flexible instrument, from which the shape data 504 was obtained, is expected to be inserted. The expected boundary 602 represents a predefined threshold, which if exceeded by the shape data 604, causes a mitigation action to be triggered.

In some examples, the expected boundary 602 may correspond to an anatomical lumen. For example, a patient's anatomy may be mapped using various medical imaging techniques such as CT scans. As the flexible instrument is inserted into the patient's anatomy, the expected boundary 602 may be defined based on a geometry of the anatomical lumen in which a specified portion of a flexible instrument, from which the shape data 404 was obtained, currently resides.

FIG. 7A illustrates an example in which the shape data 604 remains within the expected boundary 602. While the shape data 604 is illustrated as having a slight buckle 603, that buckle does not exceed the predefined threshold as defined by the expected boundary 602. FIG. 7B, however, illustrates shape data 606 shaped such that a portion 608 of the shape exceeds the expected boundary 602. In such case, the control system (e.g., control system 414) may trigger a mitigation action. The control system may determine that the portion 608 of the shape 604 is exceeding the expected boundary 602 by comparing the shape data from the shape sensor (e.g., sensor 412) with the expected boundary 602 as defined relative to an insertion axis through a shape constraint mechanism.

Figure 8:
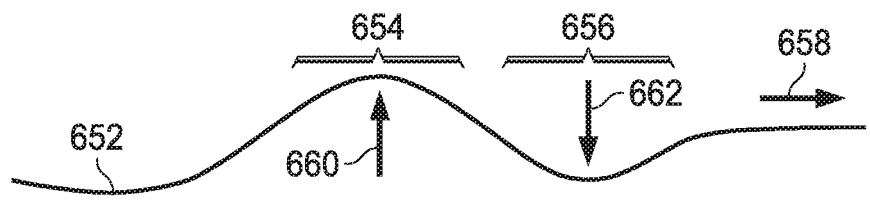
FIG. 8 illustrates directional deviation of the elongated flexible instrument from the insertion direction, according to one example of the present disclosure.

FIG. 8 illustrates directional deviation of the elongated flexible instrument 652 from an insertion direction 658 (e.g., along axis A) in order to detect buckling. Specifically, the control system may analyze shape sensor data in real time to determine if a particular portion is moving in a direction substantially orthogonal to the insertion direction 658. FIG. 8 illustrates a portion 654 of the instrument 652 that is moving in a first direction 660 substantially orthogonal to the insertion direction 658. Additionally, a portion 656 of the instrument 652 is moving in a second direction 662 that is opposite of the first direction and substantially orthogonal to the insertion direction 658. A mitigation action may be triggered if a particular portion moves in a direction 660,662 orthogonal to the insertion direction 658 for a predetermined distance or for predetermined period of time. In the present example, portion 654 may exceed the predetermined distance or period of time while portion 656 does not exceed the predetermined distance or period of time. A mitigation action may, additionally or alternatively, be triggered if a local curvature (e.g., the tightest bend radius) or cumulative curvature (e.g., the total bend angle) of the shape in the shape constraint device exceeds a particular threshold.

Figure 9:
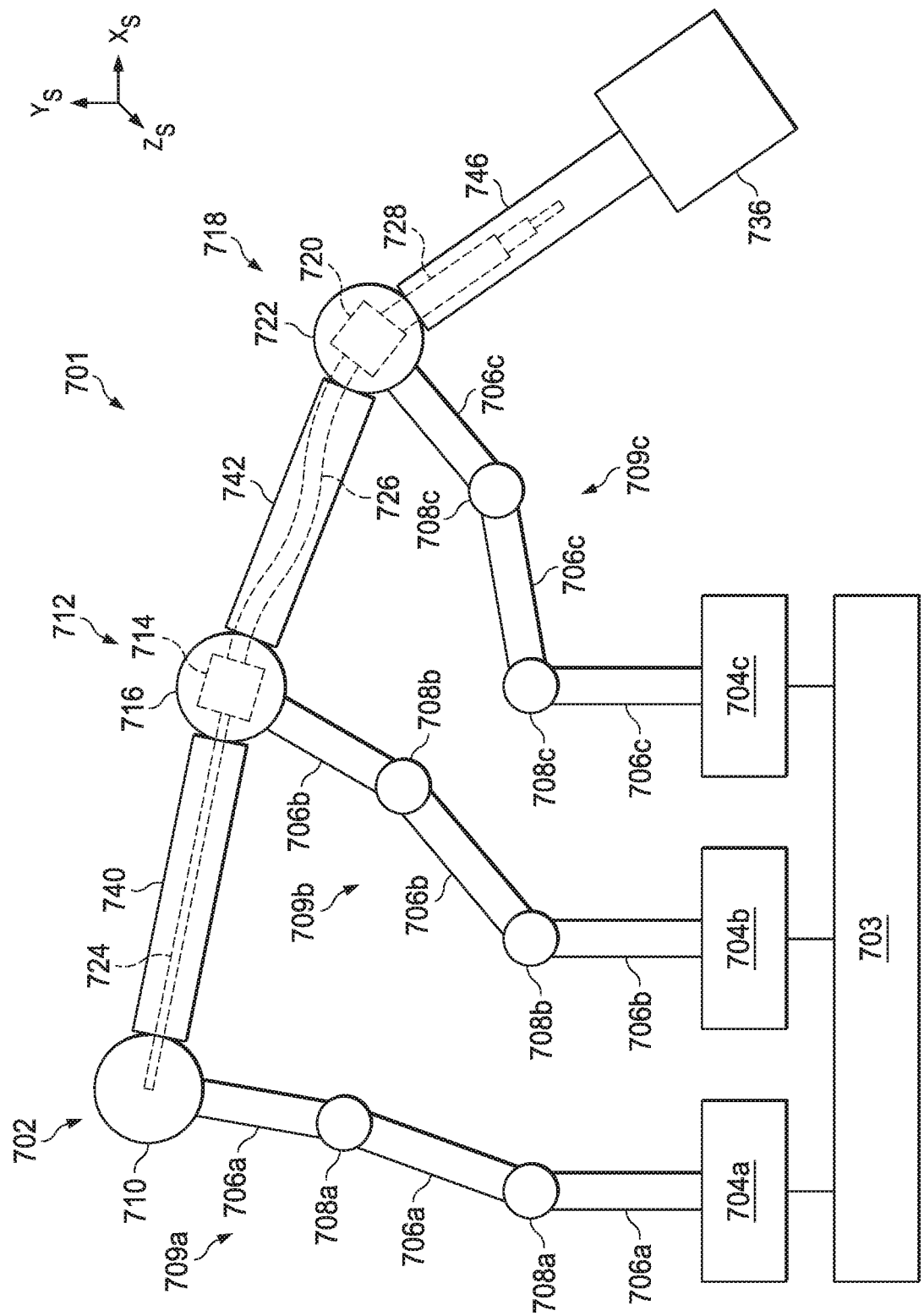
FIG. 9 illustrates a multiple instrument system that utilizes the buckling mechanisms, according to one example of the present disclosure.

FIG. 9 illustrates a multiple instrument system 701 that utilizes shape constraint devices between multiple instruments as well as between an instrument drive mechanism and entry port. The medical instrument system 701 (e.g., instruments 104, 200) includes an outer catheter 728, an inner catheter 726, and a medical tool 724. According to the present example, each medical instrument is connected to a teleoperative manipulator assembly 702, 712, 718 (e.g. manipulator assembly 102).

The manipulator assembly 702 includes a base 704a, a kinematic arm assembly 709a that includes a set of links 706a, a set of joints 708a, and an end mechanism 710. Joints 708a may include motors or other actuators to drive movement of the arm 709a in one or more degrees of freedom.

While the present example illustrates three links 706a coupled by two joints 708a, other examples may have other numbers of links 706 and joints 708. In some examples, the links may be telescoping links that can extend a predetermined distance. The links are pivotable around the joints so as to move the end mechanism to a desired position within the surgical coordinate system. Some joints may allow rotation in only one plane. Other joints may allow rotation multiple planes.

The combination of links 706a and joints 708a may provide movement of the end mechanism 710 in six degrees of freedom, which may include three degrees of linear motion (e.g., linear motion along the X, Y. Z Cartesian axes) and three degrees of rotational motion (e.g., rotation about the X, Y, Z Cartesian axes). The arms 709a may include wiring, circuitry, and other electronics to convey power and control signals from a control system 703 (e.g. control system 112) to the actuators and to instruments and instrument end effectors coupled to the end mechanism 710. Actuator position sensors such as resolvers, encoders, potentiometers, and other mechanisms may provide sensor data to the control system describing the rotation and orientation of the motor shafts. This position sensor data may be used to determine motion of the objects manipulated by the motors. For example, the joints may have sensors that may determine the rotational position of the joint or determine the angle at which the two links connecting the joint are currently positioned. Additionally, if the links are extendable, then such links may include sensors to determine the distance by which the link is currently extended. In this manner, the position of the end mechanism with respect to the base can be determined based on data from such sensors. Specifically, the control system 703 may process data received by such sensors and determine the position of the end mechanisms 710, 716, 722 with respect to their corresponding bases. Additionally, because the medical tool 724 and catheters 726, 728 may include shape and position sensors as described above, the distal end of each of the medical tool and catheters with respect to the end mechanisms may be known. Thus, the position and orientation of the distal ends of the medical tool and catheters, with respect to each other and a fixed point (e.g., one of the bases 704), within the surgical coordinate space may be determined.

The manipulator assembly 712 includes a base 704b, a kinematic arm assembly 709b that includes a set of links 706b, a set of joints 708b, and an end mechanism 716. The manipulator assembly 718 includes a base 704c, a kinematic arm assembly 709c that includes a set of links 706c, a set of joints 708c, and an end mechanism 722. The actuation and control of the assemblies 712, 718 may be substantially similar to assembly 702.

The base 704a, 704b, 704c may be portable so that each manipulator assembly can be separately positioned and fixed as desired in a surgical space near a patient. Alternatively, one or more of the manipulator assemblies may be coupled to a cart or other common platform that can be positioned in the surgical space near a patient.

In the example of FIG. 9, the medical tool 724 is connected to the end mechanism 710. Actuation of the tool 724 may be controlled, at least in part, by power and control signals via the end mechanism 710. The inner catheter 726 is connected to the end mechanism 716 by a connector mechanism 714. The connector mechanism 714 may function to guide the medical tool 724 into the inner catheter 726. Actuation of the inner catheter 726 may be controlled, at least in part, by power and control signals via the end mechanism 716. The outer catheter 728 is connected to the end mechanism 722 by a connector mechanism 720. The connector mechanism 720 may function to guide the inner catheter 726 into the outer catheter 728. Actuation of the outer catheter 728 may be controlled, at least in part, by power and control signals via the end mechanism 722. The medical tool 724 is sized and shaped to fit, slide, and rotate within the inner catheter 726. Additionally, the inner catheter 726 is sized and shaped to fit, slide, and rotate within the outer catheter 728. The inner catheter 726 and the outer catheter 728 may be similar to the catheter 202 described above and illustrated in FIG. 2A. The medical tool 724 may be one of a variety of medical tools including a biopsy tool, capture probe, ablation probe, or other surgical or diagnostic tool. In alternative embodiments, one or both of the catheters may be omitted.

The three end mechanisms 710, 716, 722 may be separately controlled to move the medical tool 724 and catheters 726, 728 as desired. For example, to insert the inner catheter 726 further into the outer catheter 728, the end mechanism 716 may be moved closer to the end mechanism 722. To insert the medical tool 724 further into both the inner catheter 726 and the outer catheter 728, the end mechanism 710 may be moved closer to the end mechanism 716.

The end mechanisms 710, 716, 722 may be moved to insert the distal end of the medical tool 724 and catheters 726, 728 into a patient's body through the entry port 736. As described above, the tool and catheters may be inserted through a natural or surgically created orifice.

A first shape constraint device 740 may be placed between the first end mechanism 710 and the second end mechanism 716. The first shape constraint device 740 thus helps reduce buckling of the medical tool 724 as it is inserted into the inner catheter 726. A second shape constraint device 742 is placed between the second end mechanism 714 and the third end mechanism 722. The second shape constraint device 742 thus helps reduce buckling of the inner catheter 726 as it is inserted into the outer catheter 728. Like the shape constraint device 308 described above, a third shape constraint device 746 is placed between the third end mechanism 720 and the entry port 736. The third shape constraint device 746 helps reduce buckling of the outer catheter 228 as it is inserted into the entry port 736. The control system 703 may utilize any of the techniques described above to define an expected shape and determine whether shape data from the medical tool 724, the inner catheter 726, or the outer catheter 728 has exceeded that defined shape. In some examples, the outer catheter 728 may serve as a shape constraint device for inner catheter 726 and inner catheter 726 may serve as a shape constraint device for tool 724. Despite being flexible, the catheters 726, 728 may be sufficiently stiff to provide support for the devices that extend through.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a non-transitory processor readable storage medium or device, including any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method comprising:
   measuring, with a sensor fixed to an elongated flexible instrument and while a distal end of the elongate flexible instrument is internal to a patient, a shape of a section of the elongated flexible instrument disposed within a shape constraint device configured to remain external to the patient;
   comparing the measured shape of the section of the elongated flexible instrument to an expected shape; and
   determining whether the measured shape of the section of the elongated flexible instrument differs from the expected shape by a predefined threshold.

2. The method of claim 1, wherein the shape of the section of the elongated flexible instrument is measured between an anatomical entryway and a proximal instrument portion.

3. The method of claim 1, wherein the expected shape is based upon the shape constraint device.

4. The method of claim 1, wherein the expected shape is an expected shape volume.

5. The method of claim 4, wherein the expected shape volume comprises one of: a substantially straight tubular volume or an arced tubular volume.

6. The method of claim 1, wherein determining whether the measured shape of the section of the elongated flexible instrument differs from the expected shape comprises determining whether a proximal portion of the section deviates from or along a reference axis more than a distal portion of the section deviates from or along the reference axis.

7. The method of claim 1, wherein determining whether the measured shape of the section of the elongated flexible instrument differs from the expected shape comprises determining whether a portion of the section moves in a predefined direction.

8. The method of claim 1, wherein the measuring the shape of the section of the elongated flexible instrument includes measuring a maximum curvature of the elongated flexible instrument.

9. The method of claim 1, wherein the measuring the shape of the section of the elongated flexible instrument includes determining a total cumulative bend angle for the section.

10. The method of claim 1, wherein a measured length of the section of the elongated flexible instrument being measured changes in real time as the elongated flexible instrument enters or retracts from an anatomical entryway.

11. The method of claim 1, further comprising, providing a notification in response to determining that the measured shape of the section of the elongated flexible instrument differs from the expected shape.

12. The method of claim 1, further comprising, in response to determining that the measured shape of the section of the elongated flexible instrument differs from the expected shape, putting the elongated flexible instrument in a safe state.

13. The method of claim 1, further comprising, in response to determining that the measured shape of the section of the elongated flexible instrument differs from the expected shape, automatically manipulating the elongated flexible instrument until a portion of the section is within the predefined threshold.

14. A method comprising:
    measuring, with a sensor secured to an elongated flexible instrument and while a distal end of the elongate flexible instrument is internal to a patient, a shape of a section of the elongated flexible instrument disposed within a shape constraint device configured to remain external to the patient;
    comparing the measured shape of the section of the elongated flexible instrument to an expected shape;
    determining whether the measured shape of the section of the elongated flexible instrument differs from the expected shape by a predefined threshold; and
    contracting the shape constraint device by advancing the elongated flexible instrument.

15. A system comprising:
    an instrument drive system;
    an elongated flexible instrument connected to the instrument drive system;
    a sensor fixed to the elongated flexible instrument and configured to measure a shape of at least a portion of the elongated flexible instrument between the instrument drive system and a distal end of the elongated flexible instrument;
    a shape constraint mechanism extending between an entry port and the instrument drive system to constrain a section of the elongated flexible instrument, the entry port being disposed distally of the shape constraint mechanism; and
    a control system configured to manipulate the elongated flexible instrument using the instrument drive system and determine whether the section of the elongated flexible instrument within the shape constraint mechanism buckles beyond a predefined threshold.

16. The system of claim 15, wherein to determine whether the section of the elongated flexible instrument within the shape constraint mechanism buckles beyond the predefined threshold, the control system is further configured to determine whether the section extends outside a boundary associated with the shape constraint mechanism.

17. The system of claim 15, wherein to determine whether the section of the elongated flexible instrument within the shape constraint mechanism buckles beyond the predefined threshold, the control system is further configured to determine whether a proximal portion of the section deviates from a reference axis more than a distal portion of the section deviates from the reference axis.

18. The system of claim 15, wherein to determine whether the section of the elongated flexible instrument within the shape constraint mechanism buckles beyond the predefined threshold, the control system is further configured to determine whether a portion of the section moves in a predefined direction away from a longitudinal axis of the shape constraint mechanism.

19. The system of claim 15, wherein the sensor comprises at least one of: a fiber-optic shape sensor, an electromagnetic sensor, optical markings, or a video camera.

20. The system of claim 15, wherein a constrained length of the section of the elongated flexible instrument being constrained changes in real time as the elongated flexible instrument moves.

* * * * *